United States Patent [19]

Cannata et al.

[11] 4,399,284

[45] Aug. 16, 1983

[54] PROCESS FOR THE OPTICAL RESOLUTION OF MIXTURES OF D- AND L-2-(6-METHOXY-2-NAPHTHYL)-PROPIONIC ACIDS

[75] Inventors: Vincenzo Cannata, Borgo Nuovo Pontecchio Marconi; Graziano Zagnoni, Vergato, both of Italy

[73] Assignee: Alfa Farmaceutici S.p.A., Bologna, Italy

[21] Appl. No.: 282,440

[22] Filed: Jul. 13, 1981

[30] Foreign Application Priority Data

Jul. 30, 1980 [IT]  Italy .................................. 3492 A/80

[51] Int. Cl.$^3$ ..................... C07D 453/04; C07B 19/00
[52] U.S. Cl. ..................................... 546/134; 562/401
[58] Field of Search ......................... 562/401; 546/134

[56] References Cited

U.S. PATENT DOCUMENTS

| | | | |
|---|---|---|---|
| 3,658,858 | 4/1972 | Harrison | 260/429 R |
| 3,658,863 | 4/1972 | Harrison | 260/438.1 |
| 3,683,015 | 8/1972 | Dyson | 562/401 |
| 3,686,183 | 8/1972 | Dyson | 546/134 |
| 3,904,682 | 9/1975 | Fried et al. | 562/401 |
| 3,988,365 | 10/1976 | Gallegra | 562/401 |

FOREIGN PATENT DOCUMENTS 2035846 12/1970 France .

OTHER PUBLICATIONS

C.A., vol. 72; 100364 (b), (1970).
C.A., vol. 74; 99717(b), (1971).
C.A., vol. 74; 3438n, (1971).
C.A., vol. 77; 5613b, (1972).
C.A., vol. 77; 88159g, (1972).
C.A., vol. 80; 14781u, (1974).

*Primary Examiner*—Natalie Trousof
*Assistant Examiner*—Vera C. Clarke
*Attorney, Agent, or Firm*—Bucknam and Archer

[57] ABSTRACT

A new process for the optical resolution of mixtures of d- and l-2-(6-methoxy-2-naphthyl)-propionic acids, which comprises preparing a solution of a mixture of d-and l-2-(6-methoxy-2-naphthyl)-propionic acids and an optically active organic base in a predetermined organic solvent, slowly cooling the obtained solution and seeding with crystals of a salt of d-2-(6-methoxy-2-naphthyl)-propionic acid with the optically active organic base containing a certain amount by weight of the organic solvent, and treating the obtained product with mineral acids in suitable organic solvents to obtain the free d-2-(6-methoxy-2-naphthyl)-propionic acid.

12 Claims, No Drawings

PROCESS FOR THE OPTICAL RESOLUTION OF MIXTURES OF D- AND L-2-(6-METHOXY-2-NAPHTHYL)-PROPIONIC ACIDS

BACKGROUND OF THE INVENTION d-2-(6-Methoxy-2-naphthyl)-propionic acid is a known substance having antiphlogistic, analgesic and antipyretic properties; it is described in U.S. Pat. No. 3,904,682. Several methods for its preparation are also known but in general, they are not stereospecific in that they first contemplate the synthesis of a racemic mixture of the d- and l-2-(6-methoxy-2-naphthyl)-propionic acids, which is subsequently resolved into the two optical antipodes through formation of salts with optically active organic bases, taking advantage from the different solubilities of the salts of the two isomers d and l with said bases in a suitable solvent (see, for instance, German application Nos. 1,934,460; 2,005,454; 2,013,641 and 2,159,011; U.S. Pat. Nos. 3,658,858 and 3,658,863.

SUMMARY OF THE INVENTION

The present invention refers to a new process for the resolution into the optically active antipodes of mixtures of d- and l-2-(6-methoxy-2-naphthyl)-propionic acids. The separation of the two optically active isomers, namely the dextrorotatory and the laevorotatory one, and, chiefly, the obtainment of the dextrorotatory isomer with satisfactory yields and purity so as to be employed in the therapy, has always represented a very difficult task, notwithstanding the apparent simplicity of the operations.

In the patent literature, several methods have been described for the resolution of mixtures of d- and l-2-(6-methoxy-2-naphthyl)-propionic acids into the corresponding optical antipodes. In any case, all of these methods possess remarkable drawbacks, which depend both on the use of volatile and dangerous solvents such as, for instance, methanol or ethanol, and the fact that the desired product ie., the dextrorotatory isomer, is obtained with the necessary purity degree only after several recrystallizations which considerably impair the final yields.

Thus, for instance, according to French application No. 2,035,846, the resolution into the optical antipodes took place by pouring a molar amount of a racemic mixture of 2-(6-methoxy-2-naphthyl)-propionic acid in methanol, heating to the boiling point for achieving complete dissolution, adding to this solution a molar amount of an optically active organic base, e.g. the cinchonidine, dissolved in methanol, heating the so obtained mixture and gradually cooling and contemporaneously seeding with previously formed crystal of a salt of d-2-(6-methoxy-2-naphthyl)-propionic acid with cinchonidine. The salt of d-2-(6-methoxy-2-naphthyl)-propionic acid, being less soluble in methanol than the corresponding laevorotatory isomer, precipitated and was recrystallized several times before being treated according to usual methods to give the desired final product ie., d-2-(6-methoxy-2-naphthyl)-propionic acid.

The drawbacks inherent to this method are self-evident: it contemplates the use of large amounts of a volatile and inflammable solvent, which must be heated until the boiling point, and several recrystallizations, which are necessary for obtaining a product with the required purity degree but, anyhow, impair the final yields: as a matter of fact, neither yield nor optical purity data are ever reported in this application.

The recrystallizations are needed because the cinchonidine salt of the dextrorotatory isomer always contains more or less relevant portions of the corresponding salt of the laevorotatory isomer.

In two subsequent publications, namely U.S. Pat. No. 3,683,015 and German application No. 2,319,245 two improved procedures for the separation of the d- and l-isomers of 2-(6-methoxy-2-naphthyl)-propionic acid were described. These procedures followed substantially the method outlined in French application No. 2,035,846, with the difference that the separation by means of the optically active organic base was carried out in the presence of a predetermined alkali agent having a $pk_a$ higher than 8. Usually, this agent was triethylamine, according to U.S. Pat. No. 3,683,015 or potassium hydroxide, according to German application No. 2,319,245. The addition of the alkali agent had the purpose of modifying the solubility so as to favor the precipitation of the salt of d-2-(6-methoxy-2-naphthyl)-propionic acid with a higher degree of purity by contemporaneously utilizing a minor amount of the predetermined optically active organic base which, incidentally, is a rather expensive compound. In any case, even following these improved procedures, one must always operate with large amounts of volatile and inflammable solvents such as, for instance, methanol. Moreover, the salt of the dextrorotatory isomer with the cinchonidine must be recrystallized several times in order to have it substantially free from the corresponding salt of the laevorotatory isomer and recover, through the usual procedures, d-2-(6-methoxy-2-naphthyl)-propionic acid with the desired purity degree.

The new process which is the object of the present invention can briefly be illustrated by the following steps:

(a) a solution of a mixture of d- and l-2-(6-methoxy-2-naphthyl)-propionic acid and an optically active organic base is prepared by dissolving, at a temperature comprised between about 70° and about 90° C., the above mixture in an organic solvent selected from formamide, monomethylformamide, dimethylformamide, monoethylformamide, diethylformamide, monomethylacetamide and dimethylacetamide, and heating the resulting mixture until complete dissolution;

(b) the so obtained hot solution is gradually cooled and, at a predetermined temperature, is seeded with crystals of a previously formed salt of d-2-(6-methoxy-2-naphthyl)-propionic acid and the optically active organic base employed in step (a), which salt contains an amount by weight of the organic solvent employed in step (a) preferably varying between about 9.5% and about 14%. Cooling is continued until the salt of the dextrorotatory isomer with the optically active organic base, owing to its minor solubility in the predetermined organic solvent precipitates, which salt still contains an amount by weight of the same organic solvent preferably varying between the above seen percent limits; the salt of the laevorotatory isomer, which is more soluble, as well as the free acid remains in the solution;

(c) the salt obtained as under (b) is treated according to known procedures, as an example with mineral acids in suitable organic solvents, to obtain the free d-2-(6-methoxy-2-naphthyl)-propionic acid.

In the actual practice according to step (a) a molar amount of a substantially racemic mixture of d- and l-2-(6-methoxy-2-naphthyl)-propionic acids and about 0.5 molar equivalents of an optically active organic base which, preferably, is the cinchonidine, are suspended in a suitable organic solvent, which preferably is an amide selected from formamide, monomethylformamide, diethylformamide, monoethylformamide, diethylformamide, monomethylacetamide and dimethylacetamide, being dimethylformamide (hereinafter referred to as DMF) and dimethylacetamide (hereinafter referred to as DMA) the most preferred ones, at a temperature comprised between about 70° and about 90° C., preferably at about 75°–80° C. The resulting solution is kept within this temperature interval for a period of time varying from about 10 to about 30 minutes, then it is slowly and gradually cooled (step b). When the temperature reaches the value of about 70°–50° C. and, preferably about 66°–60° C., the solution is seeded with crystals of a previously prepared salt of the d-2-(6-methoxy-2-naphthyl)-propionic acid with the optically active organic base which, preferably, is the cinchonidine, which salt contains an amount by weight of the predetermined amide used as the solvent such as, for instance, DMF or DMA, preferably varying between about 9.5% and about 14%. It has been found that the amount by weight may vary between about 9.5% and 12% when DMF is used and between about 10.5% and about 14% when DMA is employed.

The salt used for seeding is prepared by dissolving a molar amount of d-2-(6-methoxy-2-naphthyl)-propionic acid and a molar amount of the optically active organic base in one of the above listed amides, at a temperature comprised between about 55° and about 80° C. and slowly cooling the resulting solution to about 0° C.

The temperature at which seeding occurs may vary within sufficiently wide limits. Anyhow, the indicated interval of 70°–50° C. proved to be the most suitable one for obtaining a salt of the dextrorotatory isomer substantially free from the salt of the laevorotatory isomer.

Cooling is continued according to step (b) until a temperature comprised between about room temperature and about 0° C. is reached, whereby, owing to its minor solubility, the salt of d-2-(6-methoxy-2-naphthyl)-propionic acid with the predetermined optically active organic base precipitates, which salt still contains an amount by weight of the amide selected as the solvent varying between about 9.5% and 14%.

The so obtained product is recovered by filtration and, if desired, it may undergo a further recrystallization by using as the solvent the same amide employed in step (a) and (b) in order to remove the small amount of the salt of the laevorotatory isomer which may co-precipitate together with the salt of the desired dextrorotatory isomer. Anyhow, it has been found that this operation is not strictly necessary, as the subsequent treatment according to step (c) of the non-recrystallized salt obtained according to step (b) affords the final compound, d-2-(6-methoxy-2-naphthyl)-propionic acid with a very good yield and an excellent purity degree.

This step is carried out at room temperature, in the presence of a mineral acid such as, for instance, hydrochloric acid, and an organic solvent such as, for instance, ethyl acetate.

The process of the invention as herein described possesses remarkable advantages, if compared with the methods so far known and described in the literature. As an example, volatile and inflammable organic solvents like methanol are never used, the amounts of solvent are generally lower and also the reaction times are considerably reduced. What is more important is that the disadvantageous step regarding the subsequent recrystallizations of the salt of d-2-(6-methoxy-2-naphthyl)propionic acid with the optically active organic base for obtaining a product substantially free of the corresponding salt of the laevorotatory isomer is practically avoided, so that the desired final compound is obtained with very good yields (generally higher than 80%, calculated over the molar amount of the d-isomer contained in the racemic mixture) and a specific rotation well in agreement with the standards as provided for on page 40 of the 1978 Addendum to the British Pharmacopoeia of 1973, according to which the specific rotation of d-2-(6-methoxy-2-naphthyl)-propionic acid must be comprised between +63° and +68° (tube of 4 dm; c=1% in CHCl$_3$).

The salts of d-2-(6-methoxy-2-naphthyl)-propionic acid with the optically active organic bases containing certain amounts of the above illustrated amides used as the solvents in step (a) and (b) are new: therefore, they must be considered as a further object of the present invention.

The following examples are given only with the purpose to allow the art skilled technician to better understand and perform the present invention but in no way they must be construed as a limitation of the invention itself.

The gas-chromatographic analysis was carried out with a Parkin-Elmer F 33 apparatus. The I.R. (infrared) spectra were recorded in nujol with a Perkin-Elmer 297 spectrometer. The specific rotation was determined with a Perkin-Elmer 241 polarimeter.

EXAMPLE 1

45.05 Grams (0.2 mole) of d-2-(6-methoxy-2-naphthyl)-pronic acid and 58.87 g (0.2 mole) of cinchonidine were suspended in 400 ml of DMF at a temperature of 60° C. The temperature was brought to 80° C. until complete dissolution then the resulting solution was slowly cooled in about 3 hours to 20° C. A precipitate was obtained, which was recovered by filtration, washed with 50 ml of cold DMF and dried under vacuum at a temperature of 60° C. 110 Grams of the cinchonidine salt of d-2-(6-methoxy-2-naphthyl)-propionic acid containing 10.6% by weight of DMF (gas-chromatographic determination) were obtained. Infrared spectrum: the compound showed an absorption band at 1660 cm$^{-1}$, which is characteristic of DMF in that compound.

EXAMPLE 2

By operating substantially as described in Example 1 and employing DMA instead of DMF, it was obtained the cinchonidine salt of d-2-(6-methoxy-2-naphthyl)-propionic acid containing 11.2% by weight of DMA (gas-chromatographic determination).

Infra-red spectrum: the compound showed an absorption band at 1630 cm$^{-1}$, which is charachteristic of DMA in that compound.

EXAMPLE 3

(A) 230.26 Grams (1.0 mole) of dl-2-(6-methoxy-2-naphthyl)-propionic acid and 147.19 (0.5 mole) of cinchonidine were suspended in 1000 ml of DMF at a temperature of 75° C., the mixture was kept at this temperature for about 15 minutes, then the obtained solution was slowly cooled. At the temperature of 64° C., the solution was seeded with 2.0 g of the compound prepared as in Example 1, then cooling was continued for further 3 hours to 0° C. A precipitate was obtained, which was recovered, washed with 200 ml of cold DMF and dried under vacuum at 60° C. Yield: 247.0 g of the cinchonidine salt of d-2-(6-methoxy-2-naphthyl)-propionic acid containing 10.6% by weight of DMF (gas-chromatographic determination).

Infra-red spectrum: the compound showed an absorption band at 1660 cm$^{-1}$, which is characteristic of DMF in that compound.

(B) The product obtained as under (A) was treated under stirring at room temperature with 1500 ml of ethyl acetate and 1125 ml of 2 N hydrochloric acid. After about two hours, the organic layer was separated, washed with water to neutrality and concentrated to dryness. Yield: 93.0 g (80.7% of theoretical) of d-2-(6-methoxy-2-naphthyl)-propionic acid. M.p.: 155° C. $[\alpha]_D^{20} = 66.3°$ (c = 1% in CHCl$_3$).

EXAMPLE 4

(A) 46 Grams (0.2 mole) of dl-2-(6-methoxy-2-naphthyl)-propionic acid and 32.38 g (0.11 mole) of cinchonidine were suspended in 200 ml of DMA at 70° C. The temperature was brought to 90° C. and kept at this value for about 15 minutes until a clear solution was obtained, then the resulting solution was gradually cooled. At the temperature of 60° C., the solution was seeded with 200 mg of the compound prepared as in Example 2. The cooling was slowly continued to 54° C., whereby an abundant precipitate began to separate. The mixture was kept at this temperature for about 30 minutes, then it was further cooled to 20° C. in about 90 minutes. The obtained precipitate was recovered by filtration, washed with 50 ml of cold DMA and dried under vacuum at 60° C. Yield: 51.42 g of the cinchonidine salt of d-2-(6-methoxy-2-naphthyl)-propionic acid containing 10.9% of DMA (gas-chromatographic determination). Infra-red spectrum: the compound showed an absorption band at 1630 cm$^{-1}$, which is characteristic of DMA in that compound.

(B) By operating substantially as described in point (B) of the foregoing Example, 19.1 g (83% of theoretical) of d-2-(6-methoxy-2-naphthyl)-propionic acid were obtained. M.p.: 154°-55° C. $[\alpha]_D^{20} = 64.2°$ C. (c = 1% in CHCl$_3$).

EXAMPLE 5

230.26 Grams (1.0 mole) of dl-2-(6-methoxy-2-naphthyl)-propionic acid and 161.9 g (0.55 mole) of cinchonidine were suspended in 1000 ml of DMF at 80° C. and the mixture was kept at this temperature until a clear solution was obtained. Then the solution was gradually cooled and, at the temperature of 64° C., it was seeded with 2 g of the compound of Example 1 and further slowly cooled to 0° C. in 3 hours and a half. A dense suspension was obtained, filtered and the recovered solid was washed with 200 ml of cool DMF. It was re-suspended under stirring in 700 ml of DMF at a temperature of about 80° C., until a clear solution was obtained, then it was gradually cooled and again seeded at 64° C. with 2 g of the compound of Example 1. Cooling was slowly continued to 0° C., the obtained precipitate was recovered by filtration, washed with 150 ml of cold DMF and finally dried under vacuum at 60° C. The so obtained product was finally treated according to point B) of Example 3. Yield: 96.7 g (84.0% of theoretical) of d-2-(6-methoxy-2-naphthyl)-propionic acid. M.p. 155°-56° C. $[\alpha]_D^{20} = 68.5°$ (c = 1% in CHCl$_3$).

The following Example is provided only with the purpose of further better illustrating the inventions. It shows that without seeding with the salts of d-2-(6-methoxy-2-naphthyl)-propionic acid with the optically active organic base containing certain amounts of the amides used as the reaction solvents, the resolution into the optical antipodes does not occur.

EXAMPLE 6

A mixture of 115.17 g (0.5 mole) of dl-2-(6-methoxy-2-naphthyl)-propionic acid and 80.96 g (0.275 mole) of cinchonidine in 500 ml of DMF was heated at 75° C. for 15 minutes until complete dissolution was observed, then it was gradually cooled to 0° C. in about 3 hours. The solid precipitate which formed was recovered by filtration, washed with 100 ml of cold DMF and dried under vacuum at 60° C. 109 Grams of the cinchonidine salt of dl-2-(6-methoxy-2-naphthyl)-propionic acid practically free from DMF were obtained.

Infra-red spectrum: the absorption band at 1660 cm$^{-1}$, typical of DMF in that compound, was not observed.

The resolution into optical antipodes of the mixtures of d- and l-2-(6-methoxy-2-naphthyl)-propionic acids can also be carried out by advantageously using as the resolving agent an optically active organic base selected from 1-2-amino-1-propanol, 1-2-aminobutanol, d-2-aminobutanol, d-treo-(2-amino-1-p-nitrophenyl)-1,3-propandiol, d-anphetamine, d-menthylamine, cholestiramine, dehydroabietylamine, 1-2-benzylamino-1-propanol, d-deoxyephredin, l-ephredin, d-4-dimethylamino-3-methyl-1,2-diphenyl-2-butanol, l-4-dimethylamino-3-methyl-1,2-diphenyl-2-butanol, glucosamine, solanidine, N-methyl-d-glucamine and analogs.

We claim:

1. A process for the resolution into the optically active isomers of mixtures of d- and l-2-(6-methoxy-2-naphthyl)-propionic acids, which consists of:
    (a) preparing a solution of a mixture of d- and l-2-(6-methoxy-2-naphthyl)-propionic acids and the optically active organic base cinchonidine in an organic solvent selected from the group consisting of formamide, monomethylformamide, dimethylformamide, monoethylformamide, diethylformamide, monomethylacetamide and diethylacetamide, at a temperature between about 70° and about 90° C. to obtain a solution;
    (b) gradually cooling said solution and, at a predetermined temperature, seeding with crystals of a salt of d-2-(6-methoxy-2-naphthyl)-propionic acid and cinchonidine, said salt having a content by weight of the organic solvent used in step (a) which content is between 9.5% and about 14%, and further gradually cooling, whereby the salt of d-2-(6-methoxy-2-naphthyl)-propionic acid with cinchonidine precipitates, which salt has a content by weight of said organic solvent used in step (a) between about 9.5% and 14% and filtering said salt;
    (c) reacting said salt from step (b) with a mineral acid in an organic solvent whereby the free d-2-(6-methoxy-2-naphthyl)-propionic acid is obtained.

2. A process as defined in claim 1, wherein said organic solvent is dimethylformamide or dimethylacetamide.

3. A process as defined in claim 1, wherein about 0.5 molar equivalent of cinchonidine is reacted for each molar equivalent of said mixture of d- and l-2-(6-methoxy-2-naphthyl)-propionic acid.

4. A process as defined in claim 1, wherein the mixture of d- and l-2-(6-methoxy-2-naphthyl)-propionic acids is a substantially racemic mixture.

5. A process as defined in claim 1, wherein the seeding temperature is between about 50° and 70° C.

6. A process as defined in claim 1 wherein cooling is continued to a temperature between about room temperature and about 0° C.

7. A process as defined in claim 1, wherein the product obtained from step (b) is subjected to a further recrystallization from the same solvent.

8. A process for the resolution into the optically active isomers of a substantially racemic mixture of d- and l-2-(6-methoxy-2-naphthyl)-propionic acids which consists of:
 (a) preparing a solution of a molar equivalent of said mixture and about 0.5 molar equivalent of cinchonidine, in an organic solvent which is dimethylformamide or dimethylacetamide, at a temperature of about 75°–80° C.;
 (b) gradually cooling the obtained solution and, at a temperature between about 60° and 66° C., seeding with crystals of the cinchonidine salt of d-2-(6-methoxy-2-naphthyl)-propionic acid containing 9.5%–12% by weight of dimethylformamide or 10.5%–14% of dimethylacetamide, and continuing to cool to a temperature between about room temperature and about 0° C., whereby the cinchonidine salt of d-2-(6-methoxy-2-naphthyl)-propionic acid containing from about 9.5% to about 14% by weight of dimethylformamide or dimethylacetamide precipitates;
 (c) treating the said product from step (b) with hydrochloric acid in the presence of ethyl acetate to obtain the free d-2-(6-methoxy-2-naphthyl)-propionic acid.

9. The cinchonidine salt of d-2-(6-methoxy-2-naphthyl)-propionic acid containing 10.6% by weight of dimethylformamide.

10. The cinchonidine salt of d-2-(6-methoxy-2-naphthyl)-propionic acid containing 11.2% by weight of dimethylacetamide.

11. A process for preparing the cinchonidine salt of d-2-(6-methoxy-2-naphthyl)-propionic acid containing from about 9.5%–12% by weight of dimethylformamide or 10.5%–14% of dimethylacetamide, which consists of dissolving a molar amount of d-2-(6-methoxy-2-naphthyl)-propionic acid and a molar equivalent of cinchonidine in dimethylformamide or dimethylacetamide at a temperature between about 55° and about 65° C., slowly cooling the resulting solution to about 20° C., letting the product precipitate and filtering the product.

12. A process as defined in claim 11 wherein said solvent is dimethylacetamide and d-2-(6-methoxy-2-naphthyl)-propionic acid is reacted with cinchonidine in the molar ratio of 1:1 and the cinchonidine salt of d-2-(6-methoxy-2-naphthyl)-propionic acid having 11.2% by weight of dimethylacetamide is obtained.

* * * * *

UNITED STATES PATENT AND TRADEMARK OFFICE
CERTIFICATE OF CORRECTION

PATENT NO. : 4,399,284
DATED : August 16, 1983
INVENTOR(S) : Vincenzo Cannata and Graziano Zagnoni It is certified that error appears in the above-identified patent and that said Letters Patent are hereby corrected as shown below:

Column 3, lines 5-6, delete "diethylformamide" and substitute therefore: --dimethylformamide--.

Column 4, line 29, delete "Parkin-Elmer" and substitute therefor: --Perkin-Elmer--.

Column 6, line 7, delete "occurr" and substitute therefor: --occur--.

Column 6, lines 45-46, delete "diethylacetamide" and substitute therefor: --dimethylacetamide--.

Signed and Sealed this

Twenty-seventh Day of March 1984

[SEAL]

Attest:

GERALD J. MOSSINGHOFF

Attesting Officer   Commissioner of Patents and Trademarks